United States Patent [19]

Salome et al.

[11] Patent Number: 5,023,354

[45] Date of Patent: Jun. 11, 1991

[54] HIGH PURITY ALDITOL DIACETALS, FREE FROM ORGANIC SOLVENT TRACES AND PROCESSES FOR PREPARING SAME

[75] Inventors: Jean-Paul Salome, Vieux Berquin; Guy Fleche, Merville, both of France

[73] Assignee: Roquette Freres, Lestrem, France

[21] Appl. No.: 549,548

[22] Filed: Jul. 9, 1990

Related U.S. Application Data

[63] Continuation of Ser. No. 177,960, Apr. 5, 1988, abandoned.

[30] Foreign Application Priority Data

Apr. 7, 1987 [FR] France .................................. 87 04884

[51] Int. Cl.$^5$ ............................................ C07D 319/04
[52] U.S. Cl. ........................................................ 549/364
[58] Field of Search .......................................... 549/364

[56] References Cited

U.S. PATENT DOCUMENTS

| | | | |
|---|---|---|---|
| 4,429,140 | 1/1984 | Murai et al. ......................... | 549/370 |
| 4,562,265 | 12/1985 | Machell ................................ | 549/364 |

FOREIGN PATENT DOCUMENTS

| | | |
|---|---|---|
| 0051681 | 7/1985 | European Pat. Off. . |
| 1291819 | 10/1972 | United Kingdom . |
| 2035299 | 6/1980 | United Kingdom . |

OTHER PUBLICATIONS

"Chemical Abstracts", vol. 97, No. 15, Oct. 1982, p. 763, Abstract No. 128001w, Columbus, Ohio.
"Chemical Abstracts", vol. 104, No. 17, Apr. 2, 1986, p. 745, Abstract No. 149347s, Columbus, Ohio.
"Chemical Absracts", vol. 89, No. 19, Nov. 16, 1978, pp. 526-527, Abstract No. 163005g, Columbus, Ohio.

*Primary Examiner*—Nicky Chan
*Attorney, Agent, or Firm*—Larson and Taylor

[57] ABSTRACT

The invention is concerned with diacetals resulting of the dehyrocondensation of an alditol comprising 5 or 6 carbon atoms and a benzoic aldehyde such as in particular DBS, BEBS, BMBS or DBX, featuring a purity of at least 95% and being free of organic solvent traces, and a process for preparing the same in aqueous medium, in the presence of an acid catalyst, according to which acetalization is carried out by mixing the reactants under stirring, the reaction mixture is then neutralized by a base, then the solid phase is separated from the liquid phase and washed with warm water, wherein: the initial molar ratio of the benzoic aldehyde to the alditol is lower than 2/1, the acid catalyst is an arylsulfonic acid, the initial molar ratio of the arylsulfonic acid to the benzoic aldehyde is higher than 0.6, and the reaction temperature is lower than about 45° C.

Application specially to the clarification and stabilization of polyolefins.

17 Claims, No Drawings

HIGH PURITY ALDITOL DIACETALS, FREE FROM ORGANIC SOLVENT TRACES AND PROCESSES FOR PREPARING SAME

This application is a continuation of application Ser. No. 07/177,960 filed Apr. 5, 1988.

The invention relates to diacetals obtained by dehydrocondensing an alditol having 5 or 6 carbon atoms and a benzoic aldehyde, such as particularly dibenzylidenesorbitol or DBS, bis(para-ethylbenzylidene)sorbitol or BEBS, bis(para-methylbenzylidene)sorbitol or BMBS and dibenzylidenexylitol or DBX which feature a purity of at least 95% and are free from organic solvent traces, as well as to a process for preparing such a diacetal from an alditol having 5 or 6 carbon atoms and a benzoic aldehyde in the presence of an acid catalyst, under simple operating conditions.

According to one of its preferred aspects, the invention relates to a dibenzylidenesorbitol which features a purity of at least 95% and is free from organic solvent traces.

According to another of its preferred aspects, the invention relates to a bis(para-ethylbenzylidene)sorbitol which features a purity of at least 95% and is free from organic solvent traces.

According to another of its preferred aspects, the invention relates to a bis(para-methylbenzylidene)sorbitol which features a purity of at least 95% and is free from organic solvent traces.

According to another of its preferred aspects, the invention relates to a dibenzylidenexylitol which features a purity of at least 95% and is free from organic solvent traces.

According to the invention, the hereabove defined DBS is prepared by dehydrocondensing sorbitol and benzaldehyde in the presence of an acid catalyst.

The action of a benzoic aldehyde on an alditol having 5 or 6 carbon atoms is a reaction of acetalization catalyzed by the protons and leading, by successive dehydrocondensing operations, to the formation of the corresponding monoacetal, diacetal, and, as the case may be, triacetal.

In the case of the action of benzaldehyde on sorbitol for instance, there is successively obtained the formation of the following derivatives:

1,3-monobenzalsorbitol or monobenzylidenesorbitol (MBS), 1,3-2,4-dibenzalsorbitol or dibenzylidenesorbitol (DBS) and 1,3-2,4-5,6-tribenzalsorbitol or tribenzylidenesorbitol (TBS).

Similarly, the hereabove defined BEBS (respectively, BMBS) is prepared according to the invention by dehydrocondensing sorbitol and para-ethylbenzaldehyde (respectively para-methylbenzaldehyde) in the presence of an acid catalyst.

Similarly, the hereabove defined DBX is prepared according to the invention by dehydrocondensing xylitol and benzaldehyde in the presence of an acid catalyst.

In all the cases, the high-purity product covered by the invention is the disubstituted compound, in particular DBS, BEBS, BMBS and DBX. The mono- and tri-substituted compounds such as respectively MBS and TBS, although they may be used in certain applications are herein considered to be "impurities".

The disubstituted compounds according to the invention can be used especially as gelling agents for organic liquids or thickening agents.

As more particularly regards DBS, BEBS, BMBS and DBX among others, they can be used to confer remarkable properties on some polymers (transparency, impact strength, etc.), i.e. especially as clarifying and/or as stabilizing agents for polyolefins.

With this end in view, DBS is commonly incorporated in formulations based on polypropylene or polyethylene intended for the manufacture of transparent articles (foils, packages, containers) for food, medical or other purposes.

For technical and/or legal reasons, in the above-mentioned DBS-applications, a DBS-purity of at least 95% is generally required.

In this respect, it should be reminded that the aforesaid purity is defined as follows:

$$\text{DBS purity} = \frac{\text{mass of DBS}}{\text{mass of DBS} + \text{mass of TBS}} \times 100,$$

whereby the masses of DBS and of TBS are calculated on the dry extract obtained after separating the liquid and solid phases from the reaction medium and washing the solid phase obtained with warm water, operation which especially eliminates the possibly present residual sorbitol and MBS, without affecting DBS and TBS which are insoluble in warm water.

Whatever the processes for preparing DBS as disclosed in the prior art may be, none of them makes it possible to obtain, in a simple, economical and reproducible manner, a raw DBS having a purity of at least 95%. There is thus a need for a simple and capable of being easily implemented process, which enables raw DBS having such a purity to be obtained.

Conventionally, two types of processes for preparing DBS can be distinguished in dependence of the nature of the reaction medium: the process using at least one organic solvent and referred to as "solvent process" and the process using water as single solvent and referred to as "aqueous process".

The solvent process such as disclosed, for example, in the patent FR No. 2 065 001 seems to be capable of providing a product in which DBS would predominate by acting upon the initial molar ratio benzaldehyde/sorbitol, and it is stated that "the use of two benzaldehyde moles per sorbitol mole gives rise to a product which practically solely consists of dibenzylidenesorbitol". Such a result will seem satisfactory. However, no accurate data are given concerning the purity and the operating mode employed is complicated.

In fact, the patent FR No. 2 065 001 recommends the use of cyclohexane as reaction medium and the use of an inorganic acid catalyst.

According to this document, water would be detrimental to the speed and yield of the reaction; for that reason, it is removed by distillation of an azeotropic cyclohexane/water mixture, under continuous recycling of the cyclohexane.

The distillation of the azeotropic cyclohexane/water mixture and the recycling of the cyclohexane constitute complicated implementation steps.

The Patent EP No. 51 681 from the same Applicant discloses a process which is supposed to yield improved performances by implementing a forced stirring system, making it possible, under conditions quite close to the ones described in the aforesaid French patent (and especially a reaction temperature of the order of 70°-80° C.), to obtain a raw DBS having a purity higher than 90% and capable of reaching 99% in some particular cases.

This patent extends the use of solvents to saturated hydrocarbons and claims the imperative use of a water-soluble organic polar solvent, without which the reaction cannot practically take place. It states the indifferent use of inorganic or organic acid catalysts, the most remarkable results (purity and yield) being obtained in the presence of sulfuric acid.

However, the solvent system, based on the azeotropic removal of water, has the drawback of being rather complex and this all the more so since the polar solvent, which is indispensable and is frequently present in large amounts, must also be recovered.

The high costs resulting from the specific infrastructure required for the implementation of such a process as well as the risk of explosion, for instance, when a large amount of solvent is present, obviously result in a certain amount of drawbacks for such a system.

In brief, the "solvent process" makes it possible, at least theoretically, to obtain rather satisfactory DBS-purities, but calls for a complex and heavy implementation.

The "aqueous process" developed up to now seems to be of a relatively simpler implementation but does not result in a sufficient purity for most of the applications, that is to say a purity at least equal to 95% and, whenever possible, of 100%.

Thus, the patent FR No. 2 442 850 discloses a process for preparing DBS in aqueous medium, characterized by adding a catalyst in two steps, whereby this catalyst can be an organic or inorganic acid, along with the dilution of the reaction medium before the second step.

The first step which uses a solution of highly concentrated sorbitol must compulsorily be performed at a temperature of from 50° to 70° C. (preferably comprised between 60° and 65° C.) whereas the second step calls for the lowering of the temperature toward 15°-25° C. The switchover from one step to the other proves to be delicate and must take place at a very particular stage of the reaction.

The resulting raw DBS possesses a maximum purity which remains of the order of 90%.

It is stated that "there is used two moles of benzaldehyde per mole of sorbitol", but that this proportion can generally be comprised between 1.6 and 2.3 moles (of benzaldehyde per mole of sorbitol).

The patent application FR No. 2 486 080 discloses two operating modes for the production of DBS in aqueous phase, whereby an inorganic acid is used as catalyst. These two operating modes are implemented at room temperature (about 25° C.).

According to the first operating mode A which is not claimed, all reactants are simultaneously introduced. The best purity obtained according to this operating mode corresponds to a ratio DBS/TBS of 86/14, i.e. a DBS-purity of 86% (example 13).

According to the second operating mode B which is claimed, one succeeds in increasing the purity by adding the benzaldehyde to the aqueous reaction medium in a very gradual manner (for example in 4 hours).

According to this patent application, it is found that the DBS-purity increases when the ratio of the number of benzaldehyde moles to the number of sorbitol moles decreases with respect to the stoichiometric value of 2/1.

There is claimed a molar ratio of D-sorbitol to the aldehyde comprised between approximately 1/0.75 and approximately 1/1.75, i.e. a molar ratio of the aldehyde to D-sorbitol comprised between approximately 0.75 and 1.75.

However, with this relatively complex operating mode according to which the aldehyde is very gradually added to the aqueous reaction mixture containing the sorbitol and the inorganic acid, the formation of TBS cannot be avoided and the maximum DBS-purity is assumed to be reached with 94%. In this document, it is ascertained that the DBS-purity obtained is not satisfactory for some industrial applications and it is therefore proposed to eliminate the TBS, partly or totally, via a treatment by means of a non-polar organic solvent such as trichloro-1,1,1-ethane, which would unavoidably result in the presence of traces of this solvent in the final product.

Thus, up to now, there did not exist any process making it possible to obtain, in aqueous medium, an alditol diacetal, and especially DBS, having a purity complying with most requirements, especially regulations, i.e. a purity at least equal to 95%, without any additional purifying step with the help of an organic solvent, whereby bringing along traces of such a solvent in the final product.

In short, according to the state of the art, even by implementing complex and costly processes, alditol diacetals, particularly DBS, having a purity of at least 95% and being free from organic solvent traces could not be obtained. In fact, prior art documents, some of which suggesting the feasibility of obtaining a very pure DBS, inevitably recommend the use, during preparation or purification with a view to obtaining the required purity, of at least one organic solvent which invariably leaves traces in the final product. Consequently, none of these documents discloses the diacetals according to the invention, nor gives any indications likely to lead to obtaining same.

Intensive research carried out by the Applicant led the latter to develop a process in aqueous medium which makes it possible to obtain an alditol diacetal having such a purity, and what is more, without it being necessary to resort to several steps or to gradually add one of the reactants, for instance the aldehyde.

The Applicant has found it possible, thanks to a surprising and unexpected combination of parameters, to obtain an alditol diacetal, and especially DBS, BEBS, BMBS and DBX, in aqueous medium with comparable results, even superior to the ones commonly announced with a "solvent process".

The parameters involved in the present invention are:
the molar ratio of the aldehyde to the alditol;
the choice of the acid used as catalyst; it must be an arylsulfonic acid which is substituted or not, the inorganic acids stated as compulsory in the patent FR No. 2 486 080 being excluded since considered to be inappropriate;
the molar ratio existing between the acid and the aldehyde; and
the reaction temperature.

More precisely, an object of the invention is to provide a process for preparing a diacetal from an alditol comprising 5 or 6 carbon atoms and a benzoic aldehyde in aqueous medium, in the presence of an acid catylist, according to which acetalization is carried out by mixing the reactants under stirring, the reaction mixture is then neutralized by a base, thereafter the solid phase is separated from the liquid phase and washed with warm water, characterized in that:
- the initial molar ratio of the benzoic aldehyde to the alditol is lower than 2/1,
- the acid catalyst is an arylsulfonic acid,
- the initial molar ratio of the arylsulfonic acid to the benzoic aldehyde is higher than 0.6, and
- the reaction temperature is lower than about 45° C.

It should be reminded that by alditol, a polyol of the formula $HO-CH_2-(CHOH)_n-CH_2OH$ is meant. The alditols used according to the invention are those in which n is 3 or 4. This especially concerns sorbitol (n=4), mannitol (n=4) and xylitol (n=3).

According to the invention, as benzoic aldehyde, there can be used benzaldehyde

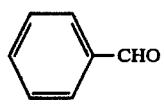

or substitution derivatives thereof, especially derivatives in which the phenyl nucleus carries at least a substituent selected from the lower alkyl groups having 1 to 4 carbon atoms, preferably the methyl group or the ethyl group.

The arylsulfonic acid can be selected within a relatively wide range of acids in which the aryl group is the phenyl group, substituted or not, or a more complex aryl group such as especially the naphthyl group and there can then be implemented naphthalene-sulfonic acid.

As preferred acids which can be used according to the invention, there can be mentioned:
paratoluenesulfonic acid (hereinafter referred to as APTS),
benzenesulfonic acid,
5-sulfosalicylic acid, and
naphthalenesulfonic acid.

The arylsulfonic acid is preferably introduced as such into the reaction system but can also be introduced in the form of a salt, preferably a sodium salt, in the presence of an inorganic acid such as hydrochloric acid, in an amount sufficient to release the required arylsulfonic acid in situ.

According to a preferred embodiment, an object of the invention is to provide a process for preparing dibenzylidenesorbitol by acetalization of sorbitol by benzaldehyde in aqueous medium, in the presence of an acid catalyst, according to which acetalization is carried out by mixing the reactants under stirring, the reaction medium is then neutralized by a base, thereafter the solid phase is separated from the liquid phase and washed with warm water, characterized in that:
- the initial molar ratio of benzaldehyde to sorbitol is lower than 2/1,
- the acid catalyst is a phenylsulfonic or naphthylsulfonic acid,
- the initial molar ratio of the phenylsulfonic acid or of the naphthylsulfonic acid to benzaldehyde is higher than 0.6, and
- the reaction temperature is lower than about 45° C.

According to another preferred embodiment, the invention relates to a process for preparing bis(paraethylbenzylidene)sorbitol [respectively bis(para-methylbenzylidene)sorbitol] by acetalization of sorbitol by para-ethyl-benzaldehyde (respectively para-methylbenzaldehyde) in aqueous medium, in the presence of an acid catalyst, according to which acetalization is carried out by mixing the reactants under stirring, the reaction mixture is then neutralized by a base, thereafter the solid phase is separated from the liquid phase and washed with warm water, characterized in that:
- the initial molar ratio of para-ethylbenzaldehyde (respectively of para-methylbenzaldehyde) to sorbitol is lower than 2/1,
- the acid catalyst is a phenylsulfonic or naphthylsulfonic acid,
- the initial molar ratio of the phenylsulfonic acid or of the naphthylsulfonic acid to para-ethylbenzaldehyde (respectively to para-methylbenzaldehyde) is higher than 0.6, and
- the reaction temperature is lower than about 45° C.

According to another preferred embodiment, the invention relates to a process for preparing dibenzylidenexylitol by acetalization of xylitol by benzaldehyde in aqueous medium, in the presence of an acid catalyst, according to which acetalization is carried out by mixing the reactants under stirring, the reaction mixture is then neutralized by a base, thereafter the solid phase is separated from the liquid phase and washed with warm water, characterized in that:
- the initial molar ratio of benzaldehyde to xylitol is lower than 2/1,
- the acid catalyst is a phenylsulfonic or naphthylsulfonic acid,
- the initial molar ratio of the phenylsulfonic acid or of the naphthylsulfonic acid to benzaldehyde is higher than 0.6, and
- the reaction temperature is lower than about 45° C.

According to a preferred embodiment of the invention, the alditol is implemented as an aqueous solution, the concentration of which does not exceed about 30% and is preferably comprised between 20 and 30%. Above 30%, the viscosity of the medium could in fact become a limiting factor for the reaction and below 20% the Applicant has verified that the reaction time was significantly increased.

According to another preferred embodiment of the invention, the quantity of benzoic aldehyde, especially of benzaldehyde, is such that the initial molar ratio benzoic aldehyde/alditol is comprised between 1/1 and 1.95/1, preferably between 1.5/1 and 1.9/1 and still preferably between 1.7/1 and 1.85/1.

Preferably, the amount of catalyst is selected in such a way that the initial molar ratio arylsulfonic acid/benzoic aldehyde is comprised between 0.6/1 and 1.5/1, preferably between 0.6/1 and 1/1.

The sequence order of introduction of the reactants and catalyst is of no significance for the present invention.

The aqueous mixture such as described above in its initial composition is brought, then maintained, under stirring, to a reaction temperature lower than about 45° C., preferably comprised between 15° and 45° C., still preferably between 20° and 40° C. and more particularly between 30° and 40° C.

The reaction time according to the invention is generally of the order of 5 to 6 hours. However, in the case of temperatures lower than approximately 20° C., it has been verified that it must be increased and this all the more so since the temperature decreases. Accordingly, in a concern of profitability and easiness of implementation of the process, one preferably resorts to a temperature at least equal to about 15° C. Anyhow, it goes without saying that the reaction temperature is selected in such a way that initially a liquid phase is always available.

The reaction medium which is in the form of an aqueous suspension is then neutralized by means of an alkaline agent such as sodium hydroxide, potassium hydroxide, sodium bicarbonate or any other agent with alkaline activity, compatible with the product prepared.

Generally, one will attempt to reach for said suspension a pH-value comprised between about 7 and 7.5, a slight excess of alkaline agent having no effect likely to be detrimental to the proper implementation of the present invention. The liquid and solid phases of the thus neutralized aqueous suspension are then separated from each other by means of any conventional means. Thus, by filtering said aqueous suspension, there is obtained a wet cake containing the diacetal, for example DBS, said cake being then subjected to at least one washing/filtering cycle.

The washing operation is preferably carried out with warm water (approximately 60° C.) and serves the purpose of removing, among others, any possible excess of alkaline agent, any residual salt likely to have formed following the neutralization of the aqueous suspension as well as any impurity of the monoacetal type, such as MBS, possibly present, or any residual alditol.

A wet cake is recovered from the final step of filtration, cake which is free from monoacetal (MBS for example) and only contains diacetal (DBS for example) and possible impurities of the triacetal type (TBS for example).

The diacetal, especially DBS, BEBS, BMBS or DBX thus prepared from an aqueous reaction medium features a remarkable purity, in all cases of at least 95%.

This product can then be dried in order to remove the residual water, then possibly ground and screened, these various operations requiring the utilization of no other means than those commonly encountered in the prior art.

As can be seen, the process of the present invention does not necessitate the presence of an organic solvent in any one of its operating steps and makes it possible, in a simple, economic and reproducible manner, to prepare an alditol diacetal, especially DBS, BEBS, BMBS or DBX, featuring such a purity that whatever the application said diacetal is intended for, any further step for purifying the same can be ignored, whereby avoiding the presence of organic solvent traces in the final product.

As will be shown from the following examples, the present invention provides, in addition to a process making it possible to obtain in a general manner DBS, BEBS, BMBS or DBX having a purity of at least 95%, according to some of its embodiments, a process for preparing an alditol diacetal in aqueous medium, according to which the resulting diacetal is free from triacetal.

Compared with the aqueous technology known in the prior art, the process according to the invention especially makes it possible to ignore:
any step in the course of which the reaction medium is brought to a temperature higher than about 45° C.,
as the case may be, any cooling step,
any deferred addition of catalyst or any continuous addition of reactant.

The following examples which relate to the preparation of diacetals according to the invention and especially of DBS are intended for illustrating and better explaining the invention. The comparative examples referred to as "comp." in the tables hereinafter are intended for evidencing the major and unexpected advantages brought about by the particular selection of the characteristics of the process according to the invention.

In the various examples of the present specification, the following definitions will be used:

Composition of the cake prior to washing: weight ratio (expressed in %) between each of the various components of the cake and the dry matter of said cake.

Diacetal purity: it can be defined as follows:

$$\text{Diacetal purity} = \frac{\text{mass of diacetal}}{\text{mass of diacetal + triacetal}} \times 100,$$

Mass yield of diacetal: it can be defined as follows:

$$\text{Mass yield of diacetal:} \frac{\text{mass of diacetal}}{\text{mass of alditol implemented}} \times 100,$$

I. INFLUENCE OF THE INITIAL MOLAR RATIO BENZOIC ALDEHYDE/SORBITOL ON THE PURITY OF THE DBS PREPARED

Common conditions:

Throughout the present research, each of the examples is carried out in accordance with the following operating conditions:
Concentration of sorbitol: 25%
Catalyst: paratoluenesulfonic acid (APTS) molar ratio acid/sorbitol = 1.25
Temperature: 30° C.
Time: 5h30.

The example described in detail below covers a particularly advantageous embodiment of the invention (example 4, table I).

The operating mode used in this example can be taken as a reference operating procedure.

DETAILED DESCRIPTION OF EXAMPLE 4 AND REFERENCE OPERATING PROCEDURE

In a cylindrical 2 l reaction vessel equipped with a double casing and a rotating stirring device fitted with a 3-bladed turbine, there are introduced 728 g of an aqueous solution of sorbitol with 25% dry matter (1 mole), 215 g of paratoluenesulfonic acid (1.25 mole) and 190.8 g of benzaldehyde (1.8 mole).

This aqueous mixture is brought, under stirring, to a temperature of 30° C., then maintained under these conditions for a duration of 5 hours and 30 minutes approximately. The reaction medium thus obtained is neutralized by a solution of 10% sodium hydroxide until a pH-value in the vicinity of 7.2 is reached, then filtered under vacuum on a filter of the BUCHNER-type.

The resulting filtration cake is then resuspended in warm water (about 60° C.), then filtered again. The product obtained, which contains approximately 50% dry matter, is then dried in a drying oven for 8 hours at a temperature of 90° C., then ground.

There is thus obtained 213.3 g of a dibenzylidenesorbitol (DBS) powder which does not contain any tribenzylidenesorbitol (TBS) (DBS-mass yield: 117.2%).

In this example 4, the molar ratio benzaldehyde/sorbitol equals 1.8. In each of the examples 1 to 3 and 5, as well as in the comparative examples 1 and 2, this ratio is made to vary.

The results obtained are collected in the following table I.

TABLE I

| Example n° | Benzaldehyde/ sorbitol (molar ratio) | COMPOSITION OF THE CAKE (%) PRIOR TO WASHING | | | | Purity of DBS % | Yield of DBS % |
|---|---|---|---|---|---|---|---|
| | | Sorbitol | MBS | DBS | TBS | | |
| 1 | 1 | 13.5 | 3.1 | 83.4 | 0 | 100 | 70.1 |
| 2 | 1.5 | 8.8 | 3.1 | 88.1 | 0 | 100 | 103.6 |
| 3 | 1.7 | 7.6 | 3.1 | 89.3 | 0 | 100 | 107.1 |
| 4 | 1.8 | 5.4 | 2.5 | 92.1 | 0 | 100 | 117.2 |
| 5 | 1.9 | 4.4 | 2.6 | 89.0 | 4.0 | 95.7 | 128.0 |
| 1 (comp.) | 2.0 | 4.4 | 0 | 90.2 | 5.4 | 94.4 | 129.6 |
| 2 (comp.) | 3.0 | 6.5 | 0 | 71.3 | 22.2 | 76.3 | 91.8 |

The results of table I show that with an initial molar ratio of benzaldehyde to sorbitol equal or superior to the stoichiometric ratio of 2, there cannot be obtained a DBS having a satisfactory purity.

Furthermore, these results show besides that for an initial molar ratio benzaldehyde/sorbitol not superior to about 1.8, the process according to the invention makes it possible to prepare DBS which is free from TBS (100% purity).

II. INFLUENCE OF INITIAL MOLAR RATIO CATALYST/BENZALDEHYDE ON THE PURITY OF THE DBS PREPARED

The tests are carried out in accordance with the aforesaid reference operating procedure, whereby the following operating conditions are adopted:
  Concentration of sorbitol: 25%
  Molar ratio: benzaldehyde/sorbitol = 1.8
  Catalyst: paratoluenesulfonic acid (APTS)
  Temperature: 30° C.
  Time: 5h30.

For each of the comparative examples 3 and 4 and examples 6 to 8 according to the invention, the catalytic ratio paratoluenesulfonic acid/benzaldehyde is made to vary. The values obtained are collected in table II hereafter.

TABLE II

| Example n° | Acid/aldehyde (molar ratio) | COMPOSITION OF THE CAKE (%) PRIOR TO WASHING | | | | Purity of DBS % | Yield of DBS % |
|---|---|---|---|---|---|---|---|
| | | Sorbitol | MBS | DBS | TBS | | |
| 3 (comp.) | 0.42 | 9.3 | 5.2 | 70.8 | 14.7 | 82.8 | 58.1 |
| 4 (comp.) | 0.55 | 10.8 | 4.2 | 76.9 | 8.1 | 90.5 | 80.0 |
| 6 | 0.64 | 5.4 | 3.7 | 90.9 | 0 | 100 | 107.7 |
| 7 | 0.69 | 5.4 | 2.5 | 92.1 | 0 | 100 | 117.2 |
| 8 | 0.77 | 4.3 | 1.8 | 93.9 | 0 | 100 | 118.0 |

The results of table II show that in order to obtain a satisfactory DBS purity, the proportion of arylsulfonic acid used must be relatively high. More precisely, the initial molar ratio arylsulfonic acid/benzoic aldehyde must at least be equal to about 0.6.

III. INFLUENCE OF THE REACTION TEMPERATURE ON THE PURITY OF THE DBS PREPARED

The tests are carried out in accordance with the aforesaid reference operating procedure, whereby the following operating conditions are adopted:
  Concentration of sorbitol: 25%
  Molar ratio benzaldehyde/sorbitol: 1.8
  Catalyst: paratoluenesulfonic acid (APTS) molar ratio: acid/sorbitol = 1.25
  Time: 5h30.

In examples 9 to 13 according to the invention and in comparative example 5, the temperature is made to vary. The values obtained are collected in table III below.

TABLE III

| Example n° | Reaction temperature °C. | COMPOSITION OF THE CAKE (%) PRIOR TO WASHING | | | | Purity of DBS % | Yield of DBS % |
|---|---|---|---|---|---|---|---|
| | | Sorbitol | MBS | DBS | TBS | | |
| 9 | 20 | 8.5 | 4.4 | 83.0 | 4.1 | 95.3 | 88.4 |
| 10 | 25 | 5.5 | 0 | 90.2 | 4.3 | 95.4 | 105.8 |
| 11 | 30 | 5.4 | 2.5 | 92.1 | 0 | 100 | 117.2 |
| 12 | 40 | 5.3 | 1.8 | 92.9 | 0 | 100 | 116.3 |
| 13 | 45 | 3.3 | 1.0 | 91.0 | 4.7 | 95.1 | 93.8 |
| 5 (comp.) | 50 | 1.9 | 0 | 68.3 | 29.8 | 69.6 | 36.1 |

The results of table III show that when the reaction temperature is higher than about 45° C., the purity of the DBS formed is not compatible with the goal of the present invention because of too high a proportion of TBS.

In return, a reaction temperature of the order of 30° to 40° C., under the aforesaid conditions, offers the remarkable possibility of becoming free from any formation of TBS and of preparing DBS of utmost purity.

In a test carried out at 15° C., after 10 hours' reaction, with the other parameters remaining unchanged, the following results have been obtained:

| Example n° | COMPOSITION OF THE CAKE (%) PRIOR TO WASHING | | | | Purity of DBS % | Yield of DBS % |
|---|---|---|---|---|---|---|
| | Sorbitol | MBS | DBS | TBS | | |
| 14 | 4.1 | 2.4 | 89 | 4.5 | 95.2 | 112.4 |

These results show that for temperatures lower than 20° C., there is obtained a satisfactory DBS purity by allowing the reaction to continue beyond 5h30.

IV. INFLUENCE OF THE CATALYST NATURE ON THE PURITY OF THE DBS PREPARED

The tests are carried out in accordance with the aforesaid reference operating procedure, whereby the following operating conditions are adopted:
Concentration of sorbitol: 25%
Molar ratio benzaldehyde/sorbitol: 1.8
Molar ratio catalyst/benzaldehyde: 0.69
Temperature: 30° C.
Time: 5h30.

In examples 15 to 19 according to the invention and in comparative examples 6 to 12, the nature of the catalyst is made to vary, that is to say the nature of the acid used. The results obtained are collected in table IV hereunder.

seems to be indispensable for the purpose of the invention.

V. INFLUENCE OF THE ALDITOL NATURE

The tests are carried out in accordance with the aforesaid reference operating procedure, whereby the following operating conditions are adopted:
Concentration of the alditol: 25%
Molar ratio benzaldehyde/alditol: 1.8
Catalyst: paratoluenesulfonic acid
Molar ratio acid/alditol: 1.25, i.e.
Molar ratio catalyst/benzaldehyde: 0.69
Temperature: 30° C.
Time: 5h30.

In examples 20 and 21 according to the invention, the nature of the alditol is made to vary.

Example 20 corresponds to the "Reference" example according to the invention (example 4 of table I, example 7 of table II, example 11 of table III and example 15

TABLE IV

| Example n° | Nature of acid | COMPOSITION OF THE CAKE (%) PRIOR TO WASHING | | | | Purity of DBS % | Yield of DBS % |
|---|---|---|---|---|---|---|---|
| | | Sorbitol | MBS | DBS | TBS | | |
| 15 | Paratoluenesulfonic | 5.4 | 2.5 | 92.1 | 0 | 100 | 117.2 |
| 16 | Benzenesulfonic | 5.3 | 0 | 94.7 | 0 | 100 | 111.6 |
| 17 | 5-sulfosalicylic | 9.2 | 0 | 90.8 | 0 | 100 | 101.0 |
| 18 | Naphthalenesulfonic | 0.7 | 0 | 99.3 | 0 | 100 | 109.0 |
| 19 | Dodecylbenzenesulfonic | 3.4 | 1.8 | 94.8 | 0 | 100 | 67.0 |
| 6 (comp.) | Methanesulfonic | 5.6 | 0 | 45.2 | 49.2 | 47.9 | 19.0 |
| 7 (comp.) | Benzoic | NO RECOVERABLE CAKE | | | | | |
| 8 (comp.) | Paranitrobenzoic | | | | | | |
| 9 (comp.) | Salicylic | | | | | | |
| 10 (comp.) | Succinic | | | | | | |
| 11 (comp.) | Orthophthalic | | | | | | |
| 12 (comp.) | Hydrochloric | 3.3 | 0 | 52.4 | 44.3 | 54.2 | 24.6 |

The results of table IV show the decisive influence of the nature of the acid catalyst used. It is particularly remarkable and surprising to ascertain that benzenesulfonic acid gives excellent results (obtaining DBS free from TBS), whereas both its alkylated homologous acid, that is to say methanesulfonic acid and its carboxylated homologous acid that is to say benzoic acid, give poor results (mixture containing a very high proportion of TBS in the one case and no recoverable cake in the other case).

It should be noted that a similar comparison can be made between 5-sulfosalicylic acid and its homologous acid not containing any sulfonic acid group, viz. salicylic acid.

Naphthalenesulfonic acid (example 18) which features a "complex" aryl grouping, makes it possible to obtain a purity as well as a DBS weight yield which can be compared with the ones obtained with paratoluenesulfonic acid (APTS) (example 15).

In return, dodecylbenzenesulfonic acid (example 19) gives a good DBS-purity, but with a relatively low weight yield. Therefore, although this acid may be used according to the invention, it is not preferred.

The simultaneous presence of an aryl group such as defined above and of a sulfonic acid group therefore of table IV).

Example 21 describes the preparation of dibenzylidenexylitol (DBX). The invention makes it possible to obtain this compound with a very high weight yield of 172% in relation to the weight of xylitol implemented.

Indeed, xylitol being an alditol having 5 carbon atoms (MW=152), it cannot give rise to the formation of triacetal, the purity after washing thus "inevitably" reaches 100%. However, emphasis must be laid on the fact that this invention makes it possible to obtain DBX with a particularly high yield, which shows that the reaction is carried out very easily and with a high selectivity [high conversion rate of xylitol and scarce building up of monoacetal].

The results obtained are collected in table V below.

TABLE V

| Example n° | Nature of alditol | COMPOSITION OF THE CAKE (%) PRIOR TO WASHING | | | | Purity of diacetal % | Yield of diacetal % |
|---|---|---|---|---|---|---|---|
| | | Alditol | acetals mono | di | tri | | |
| 20 | sorbitol | 5.4 | 2.5 | 92.1 | 0 | 100 | 117.2 |
| 21 | xylitol | 0.7 | 0 | 99.3 | 0 | 100 | 172 |

VI. INFLUENCE OF THE NATURE OF THE ALDEHYDE ON THE PREPARATION OF (SORBITOL) DIACETAL

The tests are carried out in accordance with the aforesaid reference operating procedure, whereby the following operating conditions are adopted:

Concentration of sorbitol: 25%
Molar ratio aldehyde/sorbitol: 1.8
Catalyst: paratoluenesulfonic acid (APTS)
Molar ratio acid/sorbitol: 1.25, i.e.
Molar ratio catalyst/benzaldehyde: 0.69
Temperature: 30° C.
Time: 5h30.

In examples 22 to 25 according to this invention, the nature of the aldehyde, benzaldehyde (example 22) and benzaldehyde substituted on the phenyl nucleus by at least one substituent selected from among the lower alkyl groups with 1 to 4 carbon atoms, i.e. in the present case the methyl group (example 23) and the ethyl group (example 24), either one being in para-position, or by at least a halogen, i.e. in the present case a chlorine atom in para-position (example 25).

The results obtained are collected in table VI below.

VII. INFLUENCE OF THE INITIAL MOLAR RATIO CATALYST/SUBSTITUTED BENZALDEHYDE ON THE PURITY AND YIELD OF THE DIACETAL PREPARED

The tests are carried out in accordance with the aforesaid reference operating procedure, whereby the following operating conditions are adopted:
Concentration of sorbitol: 25%
Molar ratio aldehyde/sorbitol: 1.8
Catalyst: paratoluenesulfonic acid (APTS)
Temperature: 30° C.
Time: 5h30.

In each of examples 26 to 32 according to the invention, the molar ratio paratoluenesulfonic acid/aldehyde is made to vary for the following two aldehydes: p-methylbenzaldehyde and p-ethylbenzaldehyde.

The resulting values are collected in tables VII and VIII below, respectively.

TABLE VI

| Example n° | Nature of aldehyde | COMPOSITION OF THE CAKE (%) PRIOR TO WASHING | | | | Purity of diacetal % | Yield of diacetal % |
|---|---|---|---|---|---|---|---|
| | | Sorbitol | mono | di | tri | | |
| 22 | benzaldehyde | 5.4 | 2.5 | 92.1 | 0 | 100 | 117.2 |
| 23 | P-Me benz. | 4.1 | 14.7 | 81.2 | 0 | 100 | 96.5 |
| 24 | P-Et benz. | 1.1 | 0 | 98.9 | 0 | 100 | 68.5 |
| 25 | P-Cl benz. | 0 | 82.1 | 17.9 | 0 | 100 | 32.0 |

Examples 23, 24 and 25 show that a diacetal having a purity of at least 95% (in this case 100%) can be obtained by implementing as benzoic aldehyde, a benzaldehyde substituted (in para-position) either by a methyl group (example 23) or by an ethyl group (example 24) or by a chlorine atom (example 25).

The chlorinated derivative gives a product which, prior to washing, contains a high proportion of monoacetal. The halogenated derivatives which can be used according to the invention inasmuch as they lead to a very high purity (in this case 100%) are thus not preferred owing to the low yield attainable, particularly associated with the building up of a substantial amount of monoacetal.

TABLE VII

| Example n° | Acid/p-methyl-benzaldehyde (molar ratio) | COMPOSITION OF THE CAKE (%) PRIOR TO WASHING | | | | Purity of diacetal % | Yield of diacetal % |
|---|---|---|---|---|---|---|---|
| | | Sorbitol | mono | di | tri | | |
| 26 | 0.69 | 4.1 | 14.7 | 81.2 | 0 | 100 | 96.5 |
| 27 | 0.83 | 5.4 | 0 | 94.6 | 0 | 100 | 116.9 |
| 28 | 0.97 | 8.0 | 0 | 92.0 | 0 | 100 | 125.9 |

Note:
the diacetal built up is bis(para-methylbenzylidene)sorbitol.

TABLE VIII

| Example n° | Acid/p-ethyl-benzaldehyde (molar ratio) | COMPOSITION OF THE CAKE (%) PRIOR TO WASHING | | | | Purity of diacetal % | Yield of diacetal % |
|---|---|---|---|---|---|---|---|
| | | Sorbitol | mono | di | tri | | |
| 29 | 0.69 | 1.1 | 0 | 98.9 | 0 | 100 | 68.5 |
| 30 | 0.77 | 5.2 | 0 | 94.8 | 0 | 100 | 102.2 |
| 31 | 0.83 | 4.2 | 0 | 95.2 | 0 | 100 | 120.8 |
| 32 | 0.97 | 4.05 | 0 | 95.95 | 0 | 100 | 140.0 |

Note:
the diacetal built up is bis(para-ethylbenzylidene)sorbitol.

Tables VII and VIII above show that with benzaldehyde derivatives such as those which are substituted by para-ethyl or para-methyl groups, a diacetal having a purity of at least 95% (and in this case 100%) with molar ratios catalyst (APTS)/benzoic aldehyde of 0.69 and over, can be obtained.

Furthermore, with molar ratios catalyst/aldehyde of at least 0.83, no monoacetal can in both cases be traced in the resulting cake prior to washing.

What is claimed is:

1. In a process for preparing a diacetal comprising the successive steps of
    acetalizing in an aqueous medium comprising water as single solvent and in the presence of an acid catalyst by introducing in said medium under stirring a benzoic aldehyde and an alditol having 5 or 6 carbon atoms, the initial molar ratio of the benzoic aldehyde to the alditol being lower than 2/1, neutralizing by means of a base the resulting mixture which is in the form of an aqueous suspension consisting of a solid and of a liquid phase, separating the solid phase and washing the separated solid phase with warm water, the improvement according to which the acid catalyst is selected from the group consisting of arylsulfonic acids, the arylsulfonic acid and the benzoic aldehyde are in a molar ratio which is initially higher than 0.6, and the acetalization is carried out at a temperature lower than about 45° C.

2. Process according to claim 1, wherein the alditol is introduced into the reaction medium in the form of an aqueous solution, the concentration in alditol of the latter not exceeding about 30%.

3. Process according to claim 1, wherein the alditol, when being introduced into the aqueous medium, is in aqueous solution, the concentration in alditol of the said aqueous solution being between 20 and 30%.

4. Process according to claim 1, wherein the acid catalyst is selected from the group consisting of phenylsulfonic and naphthylsulfonic acids.

5. Process according to claim 1, wherein the acid catalyst is selected from the group consisting of paratoluenesulfonic acid, benzenesulfonic acid, 5-sulfosalicylic acid and naphthalenesulfonic acid.

6. Process according to claim 1, wherein the benzoic aldehyde is benzaldehyde

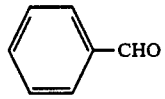

unsubstituted or substituted on the phenyl nucleus by at least one substituent selected from the group consisting of lower alkyl groups having 1 to 4 carbon atoms.

7. Process according to claim 1, wherein the benzoic aldehyde is benzaldehyde substituted on the phenyl nucleus by the methyl or the ethyl group.

8. Process according to claim 1 for preparing dibenzylidenesorbitol, wherein the alditol is sorbitol and wherein the benzoic aldehyde is benzaldehyde.

9. Process according to claim 1 for preparing bis(-para-ethylbenzylidene)sorbitol, wherein the alditol is sorbitol and wherein the benzoic aldehyde is para-ethylbenzaldehyde.

10. Process according to claim 1 for preparing bis(-para-methylbenzylidene)sorbitol, wherein the alditol is sorbitol and wherein the benzoic aldehyde is para-methylbenzaldehyde.

11. Process according to claim 1 for preparing dibenzylidenexylitol, wherein the alditol is xylitol and wherein the benzoic aldehyde is benzaldehyde.

12. Process according to claim 1, wherein the initial molar ratio arylsulfonic acid/benzoic aldehyde is between 0.6/1 and 1.5/1.

13. Process according to claim 1, wherein the initial molar ratio arylsulfonic acid/benzoic aldehyde is between 0.6/1 and 1/1.

14. Process according to claim 1, wherein the acetalization is carried out at a temperature between 15° and 45° C.

15. Process according to claim 1, wherein the acetalization is carried out at a temperature between 20° and 40° C.

16. Process according to claim 1, wherein the acetalization is carried out at a temperature between 30° and 40° C.

17. Process according to claim 1, wherein, once the acetalization has been conducted to its end, the resulting reaction medium is neutralized to a pH value between about 7 and 7.5 by means of an alkaline agent selected from the group consisting of sodium hydroxide, potassium hydroxide, sodium bicarbonate.

* * * * *